United States Patent [19]

Ishikawa et al.

[11] 4,293,553

[45] Oct. 6, 1981

[54] 1-PHTHALAZONE DERIVATIVES, AND USE THEREOF

[75] Inventors: Masayuki Ishikawa, 14-13, Akazutsumi 3-chome, Setagaya-ku, Tokyo 156, Japan; Hiromichi Tanaka, Yokohama, Japan; Yukuo Eguchi, Chiba, Japan; Shigeru Ito, Nagareyama, Japan; Yoshimi Takashima, Akishima, Japan; Masahiko Kobayashi, Kokubunji, Japan

[73] Assignee: Masayuki Ishikawa, Tokyo, Japan

[21] Appl. No.: 64,368

[22] Filed: Aug. 7, 1979

[30] Foreign Application Priority Data

Aug. 11, 1978 [JP] Japan .................................. 53-97186
Sep. 22, 1978 [JP] Japan ................................. 53-116006
Sep. 22, 1978 [JP] Japan ................................. 53-116007
Sep. 22, 1978 [JP] Japan ................................. 53-116009
Oct. 2, 1978 [JP] Japan .................................. 53-120387
Oct. 2, 1978 [JP] Japan .................................. 53-120388

[51] Int. Cl.³ .......................................... C07D 237/32
[52] U.S. Cl. .................................. 424/250; 544/237; 544/235
[58] Field of Search ................ 424/250; 544/237, 235

[56] References Cited

U.S. PATENT DOCUMENTS 3,963,716 6/1976 Inoue et al. .......................... 544/237
4,096,143 6/1978 Sato et al. ........................... 544/237

FOREIGN PATENT DOCUMENTS 49-14485 2/1974 Japan .
49-14486 2/1974 Japan .
49-18883 2/1974 Japan .
50-70352 6/1975 Japan .
50-70378 6/1975 Japan .
50-84563 7/1975 Japan .
51-16430 5/1976 Japan .
52-113986 9/1977 Japan .
52-116484 9/1977 Japan .

Primary Examiner—Nicholas S. Rizzo
Attorney, Agent, or Firm—Sherman & Shalloway

[57] ABSTRACT

Novel 1-phthalazone derivatives of the following formula

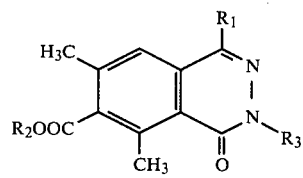

wherein $R_1$, $R_2$ and $R_3$ are as defined in claim 1, and pharmaceutically acceptable acid addition salts thereof; a process for production thereof; a pharmaceutical composition containing said compound; and a method for treating a thrombotic disease using said compound.

28 Claims, No Drawings

1-PHTHALAZONE DERIVATIVES, AND USE THEREOF

This invention relates to a novel 1-phthalazone derivative, a process for production thereof, a pharmaceutical composition containing said compound, and also to a method for treatment using said compound.

The above compound has anti-thrombotic activity, and is useful for the prevention and treatment of various diseases attributed to thromboxane $A_2$ or its metabolic precursor, arachidonic acid, such as thrombosis, transient ischemic heart attack, myocardial infarction and arterosclerosis.

More specifically, this invention pertains to 1-phthalazone derivatives of the following formula (I)

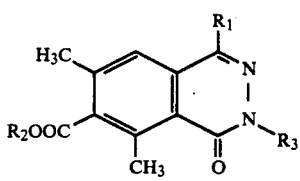

wherein
$R_1$ is a member selected from the group consisting of a hydrogen atom, alkyl groups, preferably $C_1$–$C_4$ alkyl groups, and a hydroxymethyl group,
$R_2$ is an alkyl group, preferably a $C_1$–$C_4$ alkyl group,
$R_3$ is a group of the formula

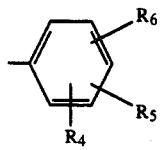

in which $R_4$ and $R_5$ are the same or different and each represents a member selected from the group consisting of a hydrogen atom, halogen atoms, lower alkyl groups, preferably $C_1$–$C_4$ alkyl groups, and lower alkoxy groups, preferably $C_1$–$C_4$ alkoxy groups, and $R_6$ represents a member selected from the group consisting of a hydrogen atom, halogen atoms, lower alkyl groups, preferably $C_1$–$C_4$ alkyl groups, lower alkoxy groups, preferably $C_1$–$C_4$ alkoxy groups, a hydroxyl group, a carboxyl group, lower alkoxycarbonyl groups, preferably $C_2$–$C_5$ alkoxycarbonyl groups, a nitro group and an amino group; or a group of the formula

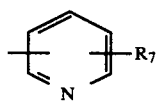

in which $R_7$ represents a hydrogen atom or a lower alkyl group, preferably a $C_1$–$C_4$ alkyl group, and pharmaceutically acceptable acid addition salts thereof; a process for preparation thereof; an antithrombotic agent containing such a compound as an active ingredient; and to a method for treating diseases attributed to thromboxane $A_2$.

It has previously been known that 4-hydroxymethyl-substituted derivatives of 7-alkoxycarbonyl-6,8-dialkyl-1-phthalazones and other 4-substituted derivatives thereof have a prophylactic action on the formation of thrombus and on arterosclerosis (U.S. Pat. No. 3,963,716).

We have now discovered that 2-substituted 1-phthalazone derivative of formula (I) above having an unsubstituted or substituted phenyl or pyridyl group at the 2-position, which are not described in the prior literature, can be synthesized, and these derivatives exhibit superior anti-thrombotic activities useful for the treatment of various thrombotic diseases attributed to thromboxane $A_2$ or its metabolic precursor, arachidonic acid.

It is an object of this invention therefore to provide novel compounds of formula (I).

Another object of this invention is to provide a process for producing novel compounds of formula (I).

Still another object of this invention is to provide use of the compounds of formula (I).

The above and other objects and advantages of this invention will become more apparent from the following description.

It has previously been known that thromboxane $A_2$ forms in the in vivo metabolic process of arachidonic acid and the thromboxane $A_2$ is a substance having strong actions of causing platelet aggregation and arterial contraction. The substance has therefore been presumed to induce thrombosis, transient ischemic heart attack, myocardial infarction and arterosclerosis. The compounds of formula (I) in accordance with this invention show superior anti-thrombotic activities, and are therefore useful for treating various thrombotic diseases.

In the compounds of formula (I), examples of suitable alkyl group are $C_1$ to $C_4$ alkyl groups such as methyl, ethyl, n- or iso-propyl, n-, iso-, sec- or tert-butyl. Examples of suitable alkoxy groups are $C_1$–$C_4$ alkoxy groups corresponding to the above-exemplified alkyl groups. Examples of suitable halogen atoms are Cl, Br and F. Examples of suitable alkoxycarbonyl groups are $C_2$–$C_5$ alkoxycarbonyl groups such as methoxycarbonyl, ethoxycarbonyl, n- or iso-propoxycarbonyl and n-, iso-, sec- or tert-butoxycarbonyl.

The compounds of formula (I) of this invention can be produced by reacting a compound of the formula (II)

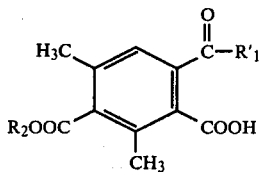

wherein $R'_1$ is a member selected from the group consisting of a hydrogen atom, alkyl groups, a hydroxymethyl group and a carboxyl group, and $R_2$ is as defined above with regard to formula (I), with a compound of the following formula (III)

$NH_2NHR_3$     (III)

wherein $R_3$ is as defined above with regard to formula (I);
and when the product is a compound of formula (I) in which $R_1$ is a carboxyl group, converting it into a reactive acid derivative and then reducing it.

A compound of formula (I) in which $R_1$ is a hydroxymethyl group, i.e. the compound of the following formula

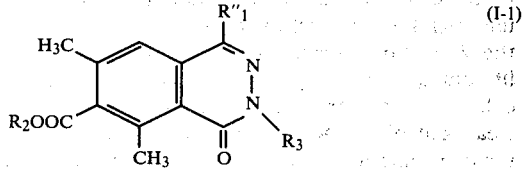

wherein $R''_1$ is a hydroxymethyl group, and $R_2$ and $R_3$ are as defined in formula (I),
can be produced by reacting a compound of the following formula (II)′

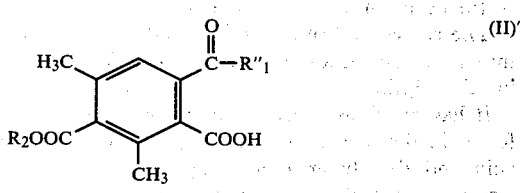

wherein $R''_1$ is a hydroxymethyl group, and $R_2$ is as defined above with regard to formula (I-1),
with a compound of the following formula (III)

wherein $R_3$ is as defind above with regard to formula (I-1);
treating the resulting product with an alkali; and then treating the product with an acid.

Compounds of formulae (II) and (II)′ in which $R'_1$ is a hydrogen atom can be expressed in the form of tautomers of the following formula (a)

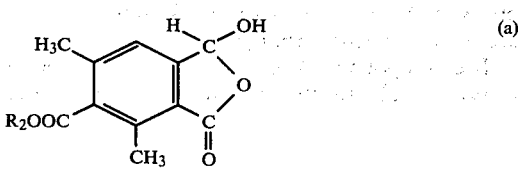

["Chemistry of Carbon Compounds", Vol. III, 834 (1956) edited by E. H. Rodds and published by Elsevier Publishing Co.]. Compounds of formulae (II) and (II)′ in which $R'_1$ is an alkyl group can be expressed in the form of tautomers of the following formula (b)

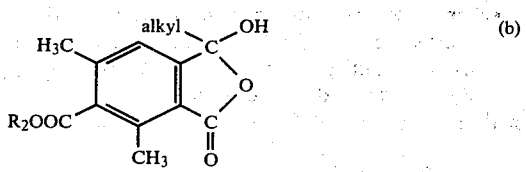

[J. Finkelstein et al., Journal of Organic Chemistry, 32, 3229 (1967)]. Compounds of formulae (II) and (II)′ in which $R'_1$ is a hydroxymethyl group can be expressed in the form of tautomers of the following formula (c) or (c)′

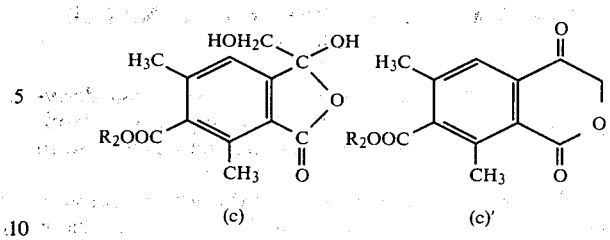

Accordingly, it should be understood that the formulae (II) and (II)′ embrace these tautomeric forms.

In the process of this invention, the reaction of a compound of formula (II) in which $R'_1$ is a hydrogen atom, an alkyl group or carboxyl group with the compound of formula (III) can be performed in a lower ($C_1$-$C_4$) aliphatic alcohol solvent such as methanol or ethanol or propanol, or in water. The reaction temperature can be chosen properly. The preferred temperature is about 30° to about 100° C. The reaction proceeds comparatively rapidly, and for example, in ethanol under reflux conditions, the reaction can be completed in about 3 to about 5 hours. If desired, the reaction may be carried out in the presence of a catalyst such as sodium acetate or potassium acetate. In the process of this invention the compound of formula (III) may be used in the form of salt, for example in the form of a mineral acid salt such as a hydrochloride or sulfate. In this case, it is preferred to use the aforesaid catalyst in an amount larger than the equivalent weight. The mole ratio between the starting compounds can be selected properly. Usually, about 1 to about 5 moles, preferably about 1 to about 2 moles, of the compound (III) is used per mole of the compound of formula (II).

In the process of this invention, the reaction between a compound of formula (II) in which $R'_1$ is a hydroxymethyl group and the compound of formula (III) can be carried out in the same way as in the case of using a compound of formula (II) in which $R'_1$ is a hydrogen atom, an alkyl group or a carboxyl group. The reaction temperature is preferably about 80° C. to about 100° C., and the reaction time is preferably about 1 to about 3 hours.

In the process of this invention, the compound of formula (I-1), which corresponds to the compound of formula (I) in which $R_1$ is hydroxymethyl, can also be produced by reacting the compound of formula (II)′ with the compound of formula (III), treating the resulting product with an alkali, and then treating the product with an acid. This reaction can be performed, for example, by reacting the reaction product between the compound of formula (II)′ and the compound (III) obtained in the above manner, with or without isolation, with about 1 to about 10 moles, preferably about 2 to about 5 moles, per mole of the reaction product, of an alkali, and then treating it with an acid to acidify the reaction mixture. Suitable alkalies include, for example, alkali metal hydroxides such as sodium hydroxide and potassium hydroxide. The reaction can be performed by using a lower alcohol such as ethanol and/or water as a solvent. Preferably, the alkali treatment is carried out at a temperature of about 80° to about 100° C. for a period of about 10 to about 50 minutes. The reaction mixture is cooled, and acidified with an acid, preferably a mineral acid such as hydrochloric acid to afford the compound of formula (I-1) corresponding to the compound of formula (I) in which $R_1$ is a hydroxymethyl group.

When the product resulting from the reaction of the compound of formula (II) with the compound of formula (III) is a compound of formula (I) in which $R_1$ is a carboxyl group, it can be converted by reduction to a compound of formula (I) in which $R_1$ is a hydroxymethyl group.

The reaction between the compound of formula (II) and the compound of formula (III), in one mode of practice, can be schematically shown as follows:

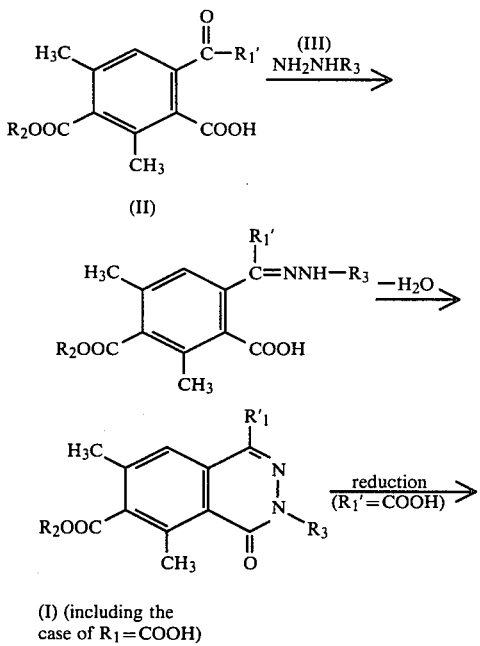

The reaction between the compound of formula (II)' and the compound of formula (III), in one mode of practice, can be schematically shown as follows:

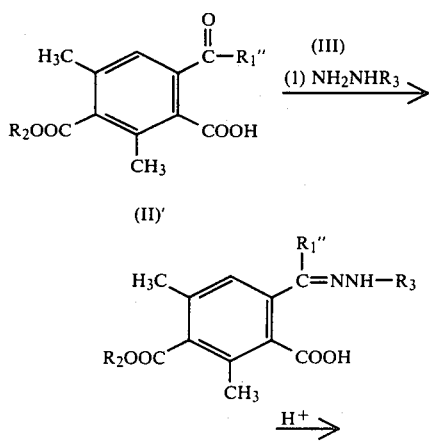

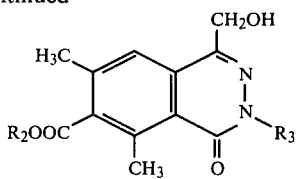

Preferably, the reduction of a compound of formula (I) in which $R_1$ is a carboxyl group is carried out after converting it into the form of a functional derivative of the carboxyl group, such as an ester, acid halide or acid anhydride.

Particularly advantageous esters include those of $C_1$-$C_4$ lower alcohols, and particularly advantageous acid halides are acid chlorides. The acid halides are moisture-sensitive and are troublesome to purify. Thus, the acid halides are preferably reduced directly without prior purification. For example, thionyl chloride is allowed to act on the carboxylic acid of formula (I) in which $R_1$ is a carboxyl group, and the excess of thionyl chloride is distilled off. The remaining acid chloride is dissolved in an inert solvent, and reduced with a borohydride complex. Especially advantageous acid anhydrides are mixed acid anhydrides between the carboxylic acid and a half ester of carbonic acid such as monoethyl carbonate or monophenyl carbonate. In this case, too, the acid anhydrides need not to be isolated or purified. For example, one may suspend the carboxylic acid in an inert organic solvent such as tetrahydrofuran, further add a dehydrochlorinating agent such as triethylamine, then add an alkyl or aryl chloroformate such as ethyl chloroformate or phenyl chloroformate to produce a mixed acid anhydride between the carboxylic acid and the half ester of carbonic acid, remove the precipitated triethylamine hydrochloride, and reduce the acid anhydride with, for example, a metal borohydride without isolating or purifying it. The reaction in this process can be schematically shown as follows with regard to the use of ethyl chloroformate.

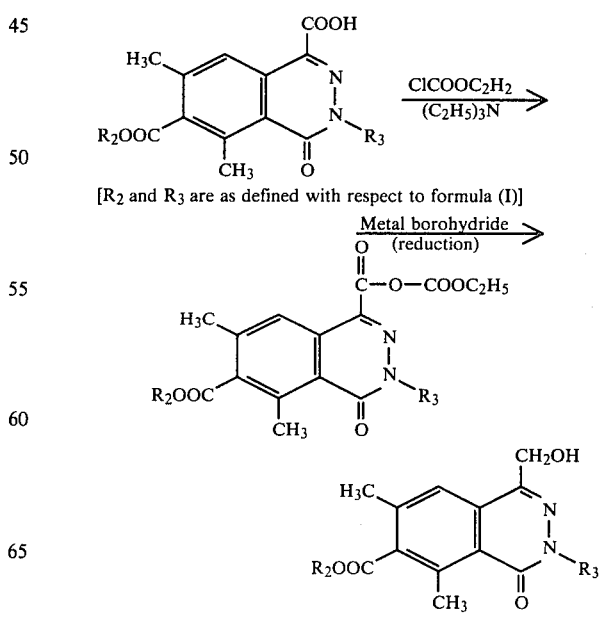

Examples of the metal borohydride used in the reducing reaction are alkali metal borohydrides and alkaline earth metal borohydrides. The alkali metal borohydrides, particularly sodium borohydride, are preferred because of their low prices. The alkaline earth metal borohydride can be used in the form of a pure reagent. Alternatively, it is possible to add an equivalent weight of an alkaline earth metal halide to a solution of sodium borohydride to form a solution of the alkaline earth metal borohydride, and to use it directly. Examples of the alkaline earth metal halide to be added include calcium chloride, magnesium bromide and magnesium chloride. The reactive derivative of the compound of formula (II), the metal borohydride and the alkaline earth metal halide may be added in any desired sequence.

In performing the process of this invention, the metal borohydride is used in an amount of, say, about 1 to 5 moles per mole of the carboxylic acid of formula (I) in which R₁ is a carboxyl group. The reaction is carried out in a solvent at a temperature of preferably from $-20°$ C. to $50°$ C. Suitable solvents include methanol, ethanol, benzene, dioxane, and tetrahydrofuran. When the functional derivative of the carboxylic acid used is an acid halide or acid anhydride, it is preferred to use the inert organic solvents rather than protic solvents.

The compound of formula (II) used in the practice of the process of this invention can be produced by various known methods.

For example, a compound of formula (II) in which $R'_1$ is a hydrogen atom can be produced by the procedure (a) shown below.

(a) The Diels-Alder adduct (1) of an alkyl isodehydroacetate and dimethyl acetylene dicarboxylate [cf. Berichte der Deutschen Chemischen Gesellschaft, 70, 1354 (1937)] is partially hydrolyzed to (2). Treatment of (2) with ethyl chloroformate in the presence of triethylamine and successive reduction with sodium borohydride afford the phthalide (3). Bromination of (3) and subsequent hydrolysis afford the o-formylbenzoic acid (4).

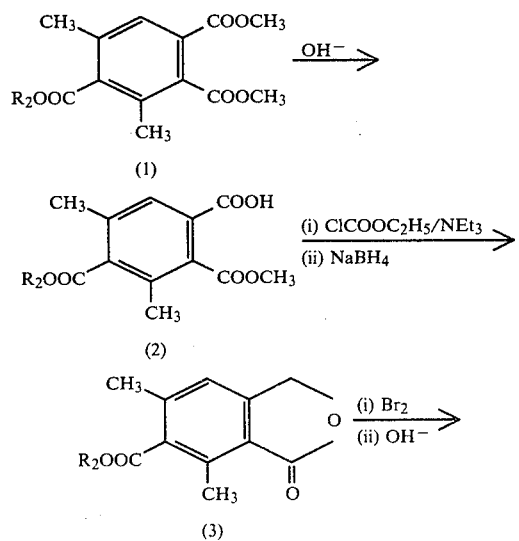

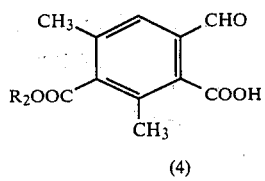

A compound of formula (II) in which $R'_1$ is an alkyl group can be produced, for example, by the following procedure (b).

(b) Heating at $80°$ to $85°$ C. of the phthalic anhydride (5) derived from (1) with malonic acid in pyridine affords the o-acetylbenzoic acid (6).

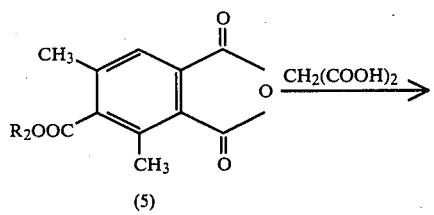

Alternatively, it can also be produced by reacting the phthalic anhydride (5) with a dialkyl cadmium.

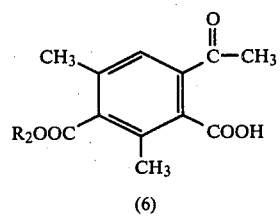

R: lower alkyl

A compound of formula (II) in which $R'_1$ is a hydroxymethyl group can be produced, for example, by the procedure (c) below.

(c) In a manner essentially analogous to that described in Ber. 40, 72 (1907) and Annual Report of Department of Pharmacy, Kanazawa University (Japan), Vol. 12, 1-6 (1961), bromination of (6) affords the o-omega-bromoacetylbenzoic acid (7) and subsequent hydrolysis yields the o-omega-hydroxyacetylbenzoic acid (8). The compound (8) can also be prepared through a diazoketone derivative in a manner analogous to that described in British patent specification No. 1,404,368.

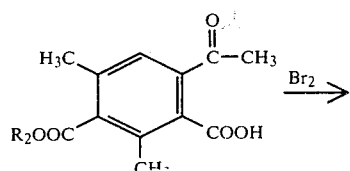

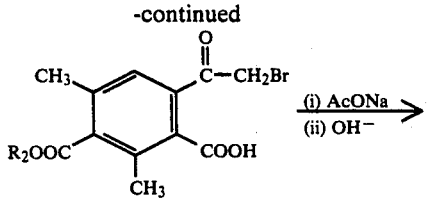

(7)

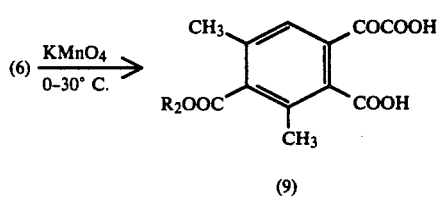

(8)

A compound of formula (II) in which $R'_1$ is a carboxyl group can be produced, for example, by the following procedure (d).

(d) Oxidation of the o-acetylbenzoic acid (6) with $KMnO_4$ in alkaline water solution at a temperature between 0° and 30° C. gives the phthalonic acid derivative (9), which can be used for subsequent reaction with the compound of formula (III) without isolation or purification.

$$(6) \xrightarrow[0-30°\ C.]{KMnO_4} \underset{(9)}{\text{CH}_3\text{-}\underset{\underset{CH_3}{|}}{\text{C}_6\text{H}}\text{(COCOOH)(COOH)(OOCR}_2)}$$

(9)

Examples of the hydrazine derivative of formula (III) used to produce the compounds of formula (I) in this invention include phenylhydrazine, o-, m- or p-tolylhydrazine, o-, m- or p-methoxyphenylhydrazine, o-, m- or p-chlorophenylhydrazine, o-, m- or p-fluorophenylhydrazine, o-, m- or p-bromophenylhydrazine, o-, m- or p-ethoxyphenylhydrazine, o-, m- or p-propoxyphenylhydrazine, 3-chloro-2-methylphenylhydrazine, 4-chloro-2-methylphenylhydrazine, 3-chloro-4-methylphenylhydrazine, 3,5-dichlorophenylhydrazine, 2,6-dichlorophenylhydrazine, 2,4-dimethoxyphenylhydrazine, 3,4-dimethoxyphenylhydrazine, 3,4-diethoxyphenylhydrazine, 3,4-methylenedioxyphenylhydrazine, 3,4,5-trimethoxyphenylhydrazine, o-, m- or p-nitrophenylhydrazine, o-, m- or p-hydrazinobenzoic acid, o-, m- or p-hydroxyphenylhydrazine, o-, m- or p-aminophenylhydrazine, 5-hydrazino-2-methoxybenzoic acid, 2-, 3- or 4-hydrazinopyridine, 2-hydrazino-3-methylpyridine, 2-hydrazino-4-methylpyridine, 3-hydrazino-2-methylpyridine, and 3-hydrazino-4-methylpyridine.

The compounds of formula (I) in accordance with this invention have low toxicity and exhibit superior anti-thrombotic activities, and are useful for preventing and treating diseases such as thrombosis, transient ischemic heart attack, myocardial infarction, and arterosclerosis.

Thus, according to this invention, there is also provided a method for treating a thrombotic disease, which comprises administering to a human or other animals an effective amount of the compound of formula (I) or its pharmaceutically acceptable acid addition salt.

There can also be provided an anti-thrombotic agent comprising an effective anti-thrombotic amount of the compound of formula (I) or its pharmaceutically acceptable acid addition salt, and a pharmaceutically acceptable carrier or diluent.

The acid addition salt can be prepared in a customary manner. Examples of the acid which forms such an acid addition salt are inorganic acids such as hydrochloric acid, hydrobromic acid and sulfuric acid.

The compounds of formula (I) or the acid addition salts thereof in accordance with this invention may be administered alone or as pharmaceutical compositions in various dosage forms suitable for oral administration such as powders, tablets, granules, capsules, troches and suspensions, and various dosage forms suitable for parenteral administration such as solutions and suspensions. The effective amount of the compound of formula (I) or its salt can be freely changed according to a particular dose intended, but usually it is from about 0.1 to about 80% based on the total amount of the carrier or diluent and the compound of formula (I) or its salt. In short, it may be any desired concentration required for administration at doses ranging from 1 to 50 mg/kg of body weight per day.

The carrier or diluent may be a pharmaceutically acceptable liquid or solid, and the term "carrier" is used in this invention to denote adjuvants as well. Examples of the liquid carrier are distilled water for injection, isotonic sodium chloride solution, Ringer's solution, Locke's solution, polyethylene glycol, ethyl alcohol, propylene glycol, glycerol and vegetable oils. The solid carrier includes, for example, sodium chloride, glucose, lactose, starch, sucrose, cetyl alcohol, cacao butter and spermaceti.

Pharmacological efficacies and acute toxicities of some compounds of formula (I) are shown below.

BIOLOGICAL TEST

Inhibitory Effect on Platelet Aggregation

From ether-anaesthetized rabbits, blood was drawn through a canule inserted into the carotid artery and collected in tubes containing 1/10 volume of sodium citrated solution (3.8% w/v). Platelet-rich plasma (PRP) was prepared by collecting the upper part of the supernatant after 15-minute centrifugation at room temperature and 150 g. An aliquot of 0.435 ml of the PRP was added to a siliconized cuvette containing a siliconized stirring bar, and placed in an aggregometer maintained at 37° C. and stirred at 1200 rpm, and then a solution of a test compound in 2.5 μl of dimethylsulfoxide at various concentrations was added and preincubated with PRP for 3 minutes. Aggregation was initiated by the addition of (10 μM, final concentration) ADP, (137 μM, final concentration) arachidonic acid, or (10 μg/ml, final concentration) collagen. Inhibitory percentage of aggregation by a test compound was calculated by the following formula $$\text{Inhibitory effect (\%)} = \frac{\Delta C - \Delta S}{\Delta C} \times 100$$

ΔC: maximum deflection in the optical density observed with a control solvent (2.5 μl of dimethylsulfoxide)

ΔS: maximum deflection in the optical density observed by a solution of a test compound Human blood was obtained from the antecubital vein of healthy human volunteers, and human platelet-rich plasma was prepared and tested in a similar manner to that in the case of rabbits described above.

The final concentrations of test compounds which showed a 50% inhibitory effect ($IC_{50}$) on platelet aggregation induced by ADP, arachidonic acid (AA), or collagen are tabulated below in Table I.

TABLE I

| | $IC_{50}$ | | | | | |
|---|---|---|---|---|---|---|
| | rabbit | | | human | | |
| Test Compound | ADP | AA | Collagen | ADP | AA | Collagen |
| 7-ethoxycarbonyl-6,8-dimethyl-4-hydroxymethyl-1-phthalazone (the compound of British Patent 1,459,606) | 32 | 22 | 36 | 35 | 28 | 42 |
| 7-ethoxycarbonyl-6,8-dimethyl-2-phenyl-1-phthalazone (the compound of the present invention) | >50 | 2.8 | 4.5 | >50 | 3.6 | 4.5 |
| 7-ethoxycarbonyl-6,8-dimethyl-2-(o-chlorophenyl)-1-phthalazone (the compound of the present invention) | >50 | 4.4 | 6.7 | >50 | 6.0 | 8.8 |
| 7-ethoxycarbonyl-6,8-dimethyl-2-(o-fluorophenyl)-1-phthalazone (the compound of the present invention) | >50 | 2.3 | 5.2 | >50 | 3.2 | 7.8 |
| 7-ethoxycarbonyl-6,8 dimethyl-4-hydroxymethyl-2-phenyl-1-phthalazone (the compound of the present invention) | >50 | 25 | 35 | >50 | 30 | 48 |
| 7-ethoxycarbonyl-6,8-dimethyl-2-(o-chlorophenyl)-4-hydroxymethy-1-phthalazone (the compound of the present invention) | >50 | 22 | 40 | >50 | 26 | 45 |

ACUTE TOXICITY

The $LD_{50}$ values of the compounds of the present invention are shown in Table II. $LD_{50}$ values were determined in mice and calculated according to the method of Litchfield and Wilcoxon described in J. Pharmacol. Exp. Ther., 96, 99 (1949).

TABLE II

| Test Compound | $LD_{50}$, mg/kg, p.o. |
|---|---|
| 7-ethoxycarbonyl-6,8-dimethyl-2-phenyl-1-phthalazone | 480 |
| 7-ethoxycarbonyl-6,8-dimethyl-2-)o-chlorophenyl)-1-phthalazone | 386 |
| 7-ethoxycarbonyl-6,8-dimethyl-2-(o-fluorophenyl)-1-phthalazone | 450 |
| 7-ethoxycarbonyl-6,8-di methyl-2-phenyl-4-hydroxymethyl-1-phthalazone | 540 |
| 7-ethoxycarbonyl-6,8-dimethyl-2-(o-chlorophenyl)-4-hydroxymethyl-1-phthalazone | 564 |

The following Examples illustrate the production of the compounds of this invention.

EXAMPLE 1

A solution of 2.50 g of 6-ethoxycarbonyl-5,7-dimethyl-3-hydroxyphthalide (equivalent to 5-ethoxycarbonyl-2-formyl-4,6-dimethylbenzoic acid), 2.70 g of o-chlorophenylhydrazine, and 2.50 g of sodium acetate in 100 ml of ethanol was refluxed for 5 hours. The ethanol was removed by evaporation, and the residue was diluted with water, and extracted with ethyl acetate. The ethyl acetate layer was washed successively with dilute aqueous hydrochloric acid and water, and dried over magnesium sulfate, and the solvent was evaporated. Recrystallizing the residue from ethanol-n-hexane yielded 2.78 g (78% of theory) of 7-ethoxycarbonyl-6,8-dimethyl-2-(o-chlorophenyl)-1-phthalazone melting at 125°–126° C.

EXAMPLE 2

A solution of 1.32 g of 6-ethoxycarbonyl-5,7-dimethyl-3-hydroxy-3-methylphthalide (equivalent to 2-acetyl-5-ethoxycarbonyl-4,6-dimethylbenzoic acid) and 1.62 g of phenylhydrazine in 120 ml of ethanol was refluxed for 3 hours. The ethanol was removed by evaporation, and the residue was taken up in ethyl acetate. The ethyl acetate layer was washed successively with dilute hydrochloric acid and water, and dried over magnesium sulfate, and the solvent was removed by distillation. Recrystallizing the residue from ether-n-hexane yielded 1.08 g (64% of theory) of 7-ethoxycarbonyl-4,6,8-trimethyl-2-phenyl-1-phthalazone melting at 109°–110° C.

EXAMPLE 3

A solution of 396 mg of 6-ethoxycarbonyl-5,7-dimethyl-3-hydroxy-3-methylphthalide and 327 mg of 3-hydrazinopyridine in 30 ml of ethanol was refluxed under nitrogen atmosphere for 3 hours. The ethanol as removed by evaporation, and the residue was diluted with water and extracted with ethyl acetate. The ethyl acetate layer was dried over magnesium sulfate and evaporated. The resulting residue was recrystallized from methanol to yield 293 mg (58% of theory) of 7-ethoxycarbonyl-4,6,8-trimethyl-2-(3-pyridyl)-1-phthalazone melting at 127°–129° C.

EXAMPLES 4–32

In a similar manner to Examples 1 to 3, the following compounds of formula (I) were obtained in a 60–90% yield as shown in Table III.

TABLE III

| | Compound of formula (I) wherein R is ethyl | | Melting point (°C.) | Recrystallization solvent |
|---|---|---|---|---|
| No. | $R_1$ | $R_3$ | | |
| 4 | H | phenyl | 138–139.5 | ethanol-n-hexane |
| 5 | H | p-methoxyphenyl | 100–101 | methanol |
| 6 | H | p-chlorophenyl | 150–151 | " |
| 7 | H | p-fluorophenyl | 131–132 | " |
| 8 | H | m-methoxyphenyl | 109–110 | " |
| 9 | H | p-tolyl | 99–100 | ethanol-n-hexane |
| 10 | H | m-tolyl | 111–113 | ethanol-n-hexane |
| 11 | H | p-bromophenyl | 158–160 | ethanol-n-hexane |
| 12 | H | 3-chloro-4-methyl-phenyl | 154–155 | methanol |
| 13 | H | 3,4-dimethoxyphenyl | 178–179 | " |

TABLE III-continued

| No. | R₁ | R₃ | Melting point (°C.) | Recrystallization solvent |
|---|---|---|---|---|
| 14 | H | 3,4,5-trimethoxyphenyl | 210–212 | ethanol |
| 15 | H | p-carboxyphenyl | 254–256 | " |
| 16 | H | p-nitrophenyl | 149–151 | " |
| 17 | H | p-aminophenyl | 133–134 | ethyl acetate-n-hexane |
| 18 | H | p-hydroxyphenyl | 161.5–162.5 | ethyl acetate-n-hexane |
| 19 | H | o-tolyl | 106–108 | ethyl ether-n-hexane |
| 20 | H | o-fluorophenyl | 116–117 | ethanol-hexane |
| 21 | methyl | m-methoxyphenyl | 131–132 | ethyl acetate-n-hexane |
| 22 | methyl | o-fluorophenyl | 123–125 | ethyl acetate-ether |
| 23 | methyl | p-tolyl | 120–121 | ethyl ether |
| 24 | methyl | m-tolyl | 105–106 | ethyl ether-n-hexane |
| 25 | methyl | p-bromophenyl | 144–145 | ethyl acetate-n-hexane |
| 26 | methyl | p-chlorophenyl | 140–141 | ethyl acetate-ether |
| 27 | methyl | 3-chloro-4-methyl-phenyl | 126–128 | ethyl acetate-ether |
| 28 | methyl | 3,4-dimethoxyphenyl | 167–169 | methanol |
| 29 | methyl | 3,4,5-trimethoxyphenyl | 197–198 | ethanol |
| 30 | H | 2-pyridyl | 131.5–132.5 | ethyl ether |
| 31 | H | 3-pyridyl | 113–115 | ethanol-water |
| 32 | methyl | 2-pyridyl | 129–130 | ethyl ether |

EXAMPLE 33

7-Ethoxycarbonyl-6,8-dimethyl-2-(p-ethoxycarbonylphenyl)-1-phthalazone melting at 167°–168° C. (recrystallized from ethanol) can be prepared by conventional esterification of the compound of Example 15 with ethanol.

EXAMPLE 34

A solution of 525 mg of 7-ethoxycarbonyl-6,8-dimethylisochroman-1,4-dione [equivalent to 5-ethoxycarbonyl-2-(ω-hydroxyacetyl)-4,6-dimethylbenzoic acid], and 297 mg of o-tolylhydrazine in 70 ml of ethanol was refluxed for 2 hours. The reaction mixture was allowed to cool, and the precipitated crystals, which melted at 203°–204° C., were filtered off. The crystals thus obtained were added to a mixture of 10 ml of ethanol and 3 ml of 10% aqueous sodium hydroxide solution, and then the reaction mixture was heated at 90° C. for 10 minutes. The resulting clear solution was cooled to room temperature, diluted with 30 ml of water, acidified with 3 ml of conc. hydrochloric acid, and concentrated under reduced pressure. The concentrate was extracted with chloroform, and the chloroform layer was dried over sodium sulfate and evaporated. The residue was fractionated by chromatography over a column packed with silica gel, and the fractions obtained from the eluates by benzene-ethyl acetate (9:1, v/v) were recrystallized from ethanol to yield 270 mg (74% of theory) of 7-ethoxycarbonyl-6,8-dimethyl-4-hydroxymethyl-2-(o-tolyl)-1-phthalazone melting at 134°–135° C.

EXAMPLE 35

To a solution prepared from 840 mg of potassium hydroxide, 2.64 g of 6-ethoxycarbonyl-5,7-dimethyl-3-hydroxy-3-methylphthalide (=2-acetyl-5-ethoxycarbonyl-4,6-dimethylbenzoic acid), and 100 ml of water was added portionwise 3.17 g of potassium permanganate with stirring. The reaction mixture was stirred for an additional 1.5 hours, and then excessive permanganate was decomposed by the addition of ethanol. The precipitated manganese dioxide was filtered off, washed thoroughly with water. The filtrates and washings were combined, and 2.37 g of p-tolylhydrazine hydrochloride and 50 ml of ethanol were added. The resulting solution was stirred at room temperature for 3 days, then saturated with carbon dioxide gas, and extracted with chloroform. The water layer was acidified with conc. hydrochloric acid, and extracted with ethyl acetate. The extracts were combined and dried over sodium sulfate. Evaporation of the organic solvent and recrystallization from ethanol-n-hexane yielded 2.37 g (62.3% of theory) of 7-ethoxycarbonyl-6,8-dimethyl-4-carboxy-2-(p-tolyl)-1-phthalazone melting at 208°–209° C. The crystals thus obtained were esterified by refluxing for 2 hours with a solution prepared from 20 ml of absolute ethanol and 2 ml of conc. sulfuric acid. Conventional work-up of the reaction mixture yielded 1.78 g of 4,7-diethoxycarbonyl-6,8-dimethyl-2-(p-tolyl)-1-phthalazone melting at 120°–122° C. (recrystallized from ethanol-n-hexane).

The crystals of the diester (2 g) described above were dissolved in 80 ml of absolute ethanol, cooled to −5°–0° C. To the stirred solution was added dropwise a solution of 350 mg of sodium borohydride in 20 ml of absolute ethanol. The reaction mixture was stirred for an additional 5 hours and then acidified with dilute acetic acid. Evaporation of the solvent, dilution with water and recrystallization of the precipitates from ethyl acetate-n-hexane yielded 1.52 g (83% of theory) of 7-ethoxycarbonyl-6,8-dimethyl-4-hydroxymethyl-2-(p-tolyl)-1-phthalazone melting at 167°–168° C.

Alternatively, 4-carboxy-7-ethoxycarbonyl-6,8-dimethyl-2-(p-tolyl)-1-phthalazone (720 mg) described above was refluxed for 2 hours with 12 ml of thionyl chloride. The excessive thionyl chloride was removed by evaporation, and the residue was dissolved in 5 ml of dioxane, and then a solution of 300 mg of sodium borohydride in 10 ml of dioxane was added dropwise at 5°–10° C. with stirring. After additional stirring for 2 hours, the reaction mixture was worked up in usual manner to yield 565 mg (81.5% of theory) of 7-ethoxycarbonyl-6,8-dimethyl-4-hydroxymethyl-2-(p-tolyl)-1-phthalazone.

EXAMPLES 36–58

In a similar manner to Example 34 or 35, the following compounds of formula (I) as shown in Table IV were obtained in a 50–80% yield.

TABLE IV

| No. | R₁ | R₃ | Melting point (°C.) | Recrystallization solvent |
|---|---|---|---|---|
| 36 | CH₂OH | phenyl | 145–146 | ethanol |
| 37 | " | o-methoxyphenyl | 165–167 | " |
| 38 | " | p-carboxyphenyl | 248–258 | " |
| 39 | " | m-tolyl | 116–117 | ethyl acetate-n-hexane |
| 40 | " | o-fluorophenyl | 147–148 | ethanol |
| 41 | " | m-fluorophenyl | 109–110 | ethyl acetate-hexane |
| 42 | " | p-fluorophenyl | 170–171 | |
| 43 | CH₂OH | m-chlorophenyl | 127–128 | methanol |
| 44 | " | p-chlorophenyl | 179–180 | " |
| 45 | " | p-bromophenyl | 188–190 | ethanol |
| 46 | " | p-methoxyphenyl | 174–176 | " |
| 47 | " | 3-chloro-4-methyl- | 147–149 | " |

TABLE IV-continued

| No. | Compound of formula (I) wherein $R_2$ is ethyl | | Melting point (°C.) | Recrystallization solvent |
|---|---|---|---|---|
| | $R_1$ | $R_3$ | | |
| | | phenyl | | |
| 48 | " | 3,5-dichlorophenyl | 140–141 | methanol |
| 49 | " | o-tolyl | 134–135 | ethanol |
| 50 | " | p-nitrophenyl | 181–182 | " |
| 51 | " | m-methoxyphenyl | 120–121 | " |
| 52 | " | p-tolyl | 167–168 | ethyl acetate-n-hexane |
| 53 | " | o-chlorophenyl | 151–152 | acetone |
| 54 | " | 3-chloro-2-methyl-phenyl | 193–194 | methanol |
| 55 | " | 4-chloro-2-methyl-phenyl | 181–182 | ethanol |
| 56 | " | 3,4,5-trimethoxy-phenyl | 204–205 | " |
| 57 | " | 2-pyridyl | 160–162 | acetone |
| 58 | " | 3-pyridyl | 189–190 | ethanol-water |

EXAMPLES 59–60

7-Ethoxycarbonyl-6,8-dimethyl--2-(p-ethoxycarbonylphenyl)-4-hydroxymethyl-1-phthalazone melting at 164°–165° C. (recrystallized from ethanol) can be prepared by conventional esterification of the compound of Example 38 with ethanol-$H_2SO_4$, and 7-ethoxycarbonyl-6,8-dimethyl-2-(p-aminophenyl)-4-hydroxymethyl-1-phthalazone melting at 211°–212° C. (recrystallized from ethanol) can be prepared by conventional catalytic reduction of the compound of Example 50 with platinum oxide in hydrogen atmosphere.

What is claimed is:

1. 1-Phthalazone derivatives of the following formula:

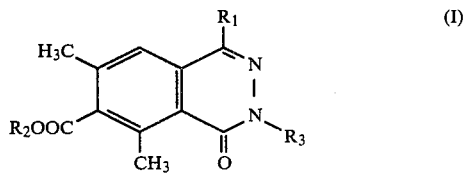

wherein
$R_1$ is a member selected from the group consisting of a hydrogen atom, alkyl groups having 1 to 4 carbon atoms and a hydroxymethyl group,
$R_2$ is an alkyl group having 1 to 4 carbon atoms, and
$R_3$ is a group having the formula

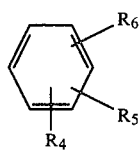

in which $R_4$ and $R_5$ are identical or different and each represents a member selected from the group consisting of a hydrogen atom, halogen atoms, alkyl groups having 1 to 4 carbon atoms and alkoxy groups having 1 to 4 carbon atoms, and $R_6$ represents a member selected from the group consisting of a hydrogen atom, halogen atoms, alkyl groups having 1 to 4 carbon atoms, alkoxy groups having 1 to 4 carbon atoms, a hydroxyl group, a carboxyl group, alkoxycarbonyl groups having 2 to 5 carbon atoms, a nitro group and an amino group; or a group having the formula

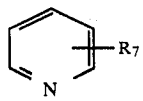

in which $R_7$ represents a hydrogen atom or an alkyl group having 1 to 4 carbon atoms;
and pharmaceutically acceptable inorganic acid addition salts thereof.

2. The compound of claim 1, wherein said compound is 7-ethoxycarbonyl-6,8-dimethyl-2-phenyl-1-phthalazone.

3. The compound of claim 1, wherein said compound is 7-ethoxycarbonyl-6,8-dimethyl-2-(o-chlorophenyl)-1-phthalazone.

4. The compound of claim 1, wherein said compound is 7-ethoxycarbonyl-6,8-dimethyl-2-(o-fluorophenyl)-1-phthalazone.

5. An anti-thrombotic agent comprising (1) a 1-phthalazone derivative of the following formula (I)

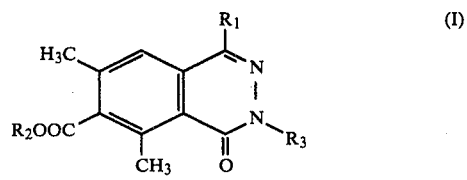

wherein
$R_1$ is a member selected from the group consisting of a hydrogen atom, alkyl groups having 1 to 4 carbon atoms and a hydroxymethyl group,
$R_2$ is an alkyl group having 1 to 4 carbon atoms, and
$R_3$ is a group having the formula

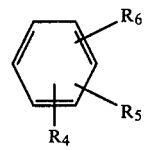

in which $R_4$ and $R_5$ are identical or different and each represents a member selected from the group consisting of a hydrogen atom, halogen atoms, alkyl groups having 1 to 4 carbon atoms and alkoxy groups having 1 to 4 carbon atoms, and $R_6$ represents a member selected from the group consisting of a hydrogen atom, halogen atoms, alkyl groups having 1 to 4 carbon atoms, alkoxy groups having 1 to 4 carbon atoms, a hydroxyl group, a carboxyl group, alkoxycarbonyl group having 2 to 5 carbon atoms, a nitro group and an amino group; or a group having the formula

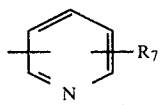

in which $R_7$ represents a hydrogen atom or an alkyl group having 1 to 4 carbon atoms;

or a pharmaceutically acceptable inorganic acid addition salt thereof, and (2) pharmaceutically acceptable carrier or diluent.

6. A method for treating a thrombotic disease, which comprises administering to a human or non-human animal subject suffering from thrombotic disease a pharmaceutically effective amount of a 1-phthalazone derivative of the following formula (I)

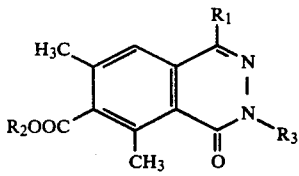

wherein
$R_1$ is a member selected from the group consisting of a hydrogen atom, alkyl groups having 1 to 4 carbon atoms and a hydroxymethyl group,
$R_2$ is an alkyl group having 1 to 4 carbon atoms, and
$R_3$ is a group having the formula

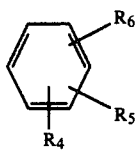

in which $R_4$ and $R_5$ are identical or different and each represents a member selected from the group consisting of a hydrogen atom, halogen atoms, alkyl groups having 1 to 4 carbon atoms and alkoxy groups having 1 to 4 carbon atoms, and $R_6$ represents a member selected from the group consisting of a hydrogen atom, halogen atoms, alkyl groups having 1 to 4 carbon atoms, alkoxy groups having 1 to 4 carbon atoms, a hydroxyl group, a carboxyl group, alkoxycarbonyl groups having 2 to 5 carbon atoms, a nitro group and an amino group; or a group having the formula

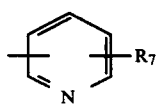

in which $R_7$ represents a hydrogen atom or an alkyl group having 1 to 4 carbon atoms;
or a pharmaceutically acceptable inorganic acid addition salt thereof.

7. 1-phthalazone derivative of claim 1 wherein $R_2$ is ethyl, $R_1$ is H, $CH_3$ or $CH_2OH$ and $R_3$ is selected from the group consisting of phenyl, methoxyphenyl, chlorophenyl, bromophenyl, fluorophenyl, tolyl, 3-chloro-4-methylphenyl, dimethoxyphenyl, trimethoxyphenyl, carboxyphenyl, nitrophenyl, aminophenyl, hydroxyphenyl and ethoxycarbonylphenyl.

8. The 1-phthalazone derivative of claim 1 wherein $R_2$ is ethyl, $R_1$ is H, $CH_3$ or $CH_2OH$ and $R_3$ is the group

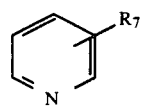

9. The 1-phthalazone derivative of claim 8 wherein $R_7$ is a hydrogen atom.

10. The method of claim 6 which comprises administering the 1-phthalazone derivative or its pharmaceutically acceptable inorganic acid addition salt at a dose ranging from 1 to 50 mg/kg of body weight per day.

11. An anti-thrombotic agent according to claim 5 wherein said 1-phthalazone derivative is 7-ethoxycarbonyl-6,8-dimethyl-2-phenyl-1-phthalazone.

12. An anti-thrombotic agent according to claim 5 wherein said 1-phthalazone derivative is 7-ethoxycarbonyl-6,8-dimethyl-2-(o-chlorophenyl)-1-phthalazone.

13. An anti-thrombotic agent according to claim 5 wherein said 1-phthalazone derivative is 7-ethoxycarbonyl-6,8-dimethyl-2-(o-fluorophenyl)-1-phthalazone.

14. An anti-thrombotic agent according to claim 5 wherein $R_2$ is ethyl, $R_1$ is H, $CH_3$ or $CH_2OH$ and $R_3$ is selected from the group consisting of phenyl, methoxyphenyl, chlorophenyl, bromophenyl, fluorophenyl, tolyl, 3-chloro-4-methylphenyl, dimethoxyphenyl, trimethoxyphenyl, carboxyphenyl, nitrophenyl, aminophenyl, hydroxyphenyl and ethoxycarbonylphenyl.

15. An anti-thrombotic agent according to claim 5 wherein $R_2$ is ethyl, $R_1$ is H, $CH_3$ or $CH_2OH$ and $R_3$ is the group

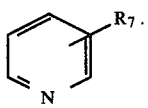

16. An anti-thrombotic agent according to claim 15 wherein $R_7$ is a hydrogen atom.

17. The method of claim 6 wherein said 1-phthalazone derivative is 7-ethoxycarbonyl-6,8-dimethyl-2-phenyl-1-phthalazone.

18. The method of claim 6 wherein said 1-phthalazone derivative is 7-ethoxycarbonyl-6,8-dimethyl-2-(o-chlorophenyl)1-phthalazone.

19. The method of claim 6 wherein said 1-phthalazone derivative is 7-ethoxycarbonyl-6,8-dimethyl-2-(o-fluorophenyl)-1-phthalazone.

20. The method of claim 6 wherein $R_2$ is ethyl, $R_1$ is H, $CH_3$ or $CH_2OH$ and $R_3$ is selected from the group consisting of phenyl, methoxyphenyl, chlorophenyl, bromophenyl, fluorophenyl, tolyl, 3-chloro-4-methylphenyl, dimethoxyphenyl, trimethoxyphenyl, carboxyphenyl, nitrophenyl, aminophenyl, hydroxyphenyl, and ethoxycarbonylphenyl.

21. The method of claim 6 wherein $R_2$ is ethyl, $R_1$ is H, $CH_3$ or $CH_2OH$ and $R_3$ is the group

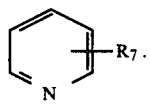

22. The method of claim 21 wherein $R_7$ is H.
23. The 1-phthalazone derivative of claim 7 wherein $R_1$ is H.
24. The 1-phthalazone derivative of claim 7 wherein $R_1$ is $CH_3$.
25. The anti-thrombotic agent according to claim 14 wherein $R_1$ is H.
26. The anti-thrombotic agent according to claim 14 wherein $R_1$ is $CH_3$.
27. The method of claim 20 wherein $R_1$ is H.
28. The method of claim 20 wherein $R_1$ is $CH_3$.

* * * * *